United States Patent [19]
Schönhöffer

[11] Patent Number: 5,571,192
[45] Date of Patent: Nov. 5, 1996

[54] PROSTHETIC VERTEBRAL IMPLANT

[75] Inventor: Helmut Schönhöffer, Ulm, Germany

[73] Assignee: Heinrich Ulrich, Ulm/Donau, Germany

[21] Appl. No.: 497,948

[22] Filed: Jul. 3, 1995

[30] Foreign Application Priority Data

Jul. 2, 1994 [DE] Germany .......................... 44 23 257.8

[51] Int. Cl.⁶ ..................................................... A61F 2/44
[52] U.S. Cl. .................. 623/17; 606/61; 606/63
[58] Field of Search ................. 623/17; 606/61, 606/63, 90; 411/383, 384, 437

[56] References Cited

U.S. PATENT DOCUMENTS

| | | | |
|---|---|---|---|
| 4,401,112 | 11/1985 | Rezaian | 606/61 |
| 4,553,273 | 8/1985 | Wu | 606/61 |
| 4,657,550 | 4/1987 | Daher | 623/17 |
| 5,192,327 | 3/1993 | Brantigan | 606/61 |

FOREIGN PATENT DOCUMENTS

| | | | |
|---|---|---|---|
| 0 268 115 | 5/1988 | European Pat. Off. | |
| 0567424 | 10/1993 | European Pat. Off. | 623/17 |
| 34 35 771 | 4/1985 | Germany | |

*Primary Examiner*—Randy C. Shay
*Attorney, Agent, or Firm*—Herbert Dubno; Andrew Wilford

[57] ABSTRACT

A spinal implant for engagement in a space left by ablation of a vertebral body between a pair of adjacent vertebrae has a tubular center element extending along an axis and a pair of end elements. The center element is formed with upper and lower screwthreads of opposite hand and with a plurality of radially throughgoing apertures. The upper and lower tubular end elements are each formed with a plurality of radially throughgoing apertures, each have a circular-section inner end threaded onto a respective one of the screwthreads, and each have an outer end adapted to bear on a respective one of the adjacent vertebrae.

18 Claims, 3 Drawing Sheets

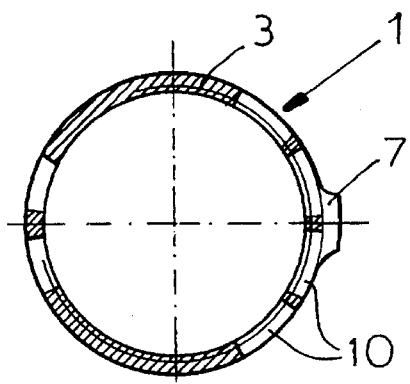
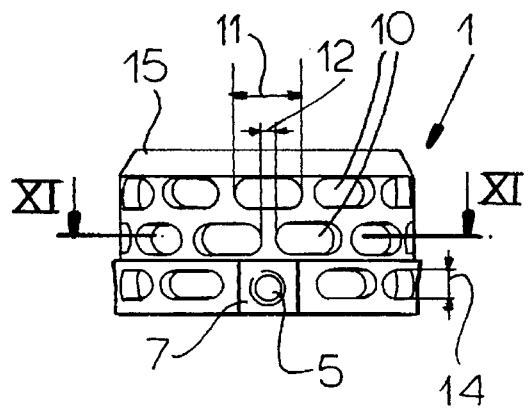
FIG.9  FIG.10
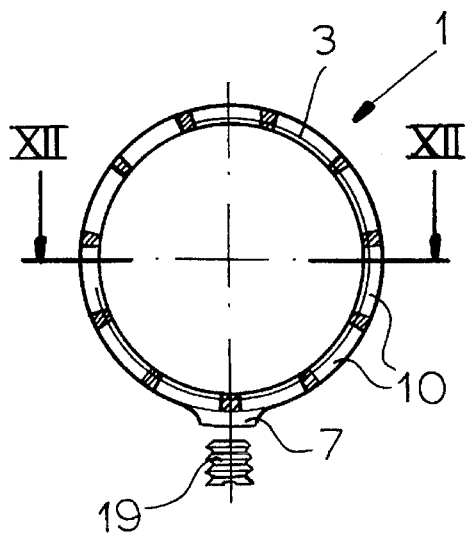
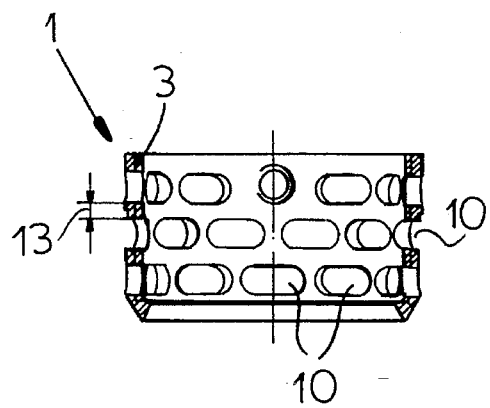
FIG.11  FIG.12

PROSTHETIC VERTEBRAL IMPLANT

SPECIFICATION

1. Field of the Invention

The present invention relates to an implant used to replace the body or bodies or one or more vertebrae. More particularly this invention concerns a prosthetic vertebral implant employed after the ablation of the body or bodies of one or more vertebra to prevent spinal collapse.

2. Background of the Invention

When a vertebra is broken or crushed it is frequently necessary to ablate the body of the crushed or broken vertebra or vertebra. In order, however, to prevent the spinal column from collapsing with damage to the fragile spinal cord running in the vertebral foramen forward of the vertebral body, it is necessary to employ a spacer. This device is braced vertically between the bodies of the adjacent vertebra and holds them apart at the desired spacing.

In one system described in U.S. Pat. No. 4,657,550 of Daher upper and lower sockets are mounted on the vertebrae above and below the ablated vertebra or vertebrae, and an extensible element is fitted between them. This extensible element in turn is formed by two plugs adapted to fit into the sockets and themselves threaded in respective ends of a center sleeve, with the upper screwthreads being of an opposite hand to the lower screw-threads so that rotation of the center sleeve in one direction extends the element and allows it to bring pressure to bear, upward and downward, on the adjacent vertebrae.

The disadvantage of this system is that it is not readily incorporated in the spinal structure when bone regrowth occurs. While German 3,431,771 proposes an implant that is aimed at encouraging regrowth, it is not aimed at this type of spinal implant or readily adaptable to the above-described system.

European patent document 0,268,115 of Biederman has a perforated metal sleeve used as brace. Such an arrangement is very hard to fit accurately, and does not allow the space to be expanded for distraction as is frequently necessary in spinal injuries.

3. Objects of the Invention

It is therefore an object of the present invention to provide an improved spinal implant.

Another object is the provision of such an improved spinal implant which overcomes the above-given disadvantages, that is which can be installed easily and used for spreading the adjacent vertebrae, and which also encourages bone regrowth.

SUMMARY OF THE INVENTION

A spinal implant for engagement in a space left by ablation of a vertebral body between a pair of adjacent vertebrae has according to the invention a tubular center element extending along an axis and a pair of end elements. The center element is formed with upper and lower screwthreads of opposite hand and with a plurality of radially throughgoing apertures. The upper and lower tubular end elements are each formed with a plurality of radially throughgoing apertures, each have a circular-section inner end threaded onto a respective one of the screwthreads, and each have an outer end adapted to bear on a respective one of the adjacent vertebrae.

Thus such an implant can be set in an area where the body of bodies of one or more vertebra have been ablated. The length of the implant is then increased by rotating the center element to force out the end elements and bring their outer ends into solid engagement with the confronting vertebral surfaces. The screwthreads offer sufficient mechanical advantage that the system can even be used to distract the vertebrae, as is frequently necessary in the event of a crushing injury to a vertebra. The tubular elements of the implant can be filled with bone cement and/or bone fragments to ensure that the implant becomes anchored in place in living bone. Since the outer elements surround the screwthreads of the inner element, once installed the screwthreads will be largely covered so that their sharp edges do not impair healing.

The inner ends of the end elements according to the invention radially surround respective upper and lower ends of the center element. At least one of the end elements is formed at its inner end with a radially throughgoing threaded bore. The implant further has according to the invention a setscrew threaded in the bore and bearing radially on the center element. Thus once the desired length is attained, the setscrew is tightened to lock the elements relative to each other. The one end element in accordance with this invention has a thickened region surrounding the bore. More particularly, this one end element is formed with a circumferential thickened region through which the bore extends.

To assist installation of the implant according to the invention the center element has between the screwthreads a thread-free portion formed with the apertures which in the thread-free portion are substantially circular. Thus a tool can be inserted into these central circular-section apertures to rotate the center element and thereby adjust the length of the assembly.

The apertures of the end elements according to this invention are elongated angularly and radially traverse the respective screwthreads. More specifically they have major axes lying in planes perpendicular to the axis. The apertures of each element are arrayed in rows each centered on a respective plane perpendicular to the axis and the apertures of each row are offset angularly from the apertures of adjacent rows. Each aperture has a major axis lying in a plane perpendicular to the axis and a minor axis parallel to the axis and each major axis is at least twice as long as the respective minor axis. The apertures are arranged in rows lying in the respective planes and the axial spacing between each row and the adjacent rows is equal to about half the axial length of the respective minor axes.

For most solid mounting of the implant in accordance with the invention the outer end of at least one of the end elements has an edge lying in a plane forming an acute angle with the axis. The outer end of at least one of the end elements can be formed with an annular array of teeth adapted to dig into the respective vertebra. In this case the outer end of the one end element is formed between the teeth with outwardly open notches. The one end is formed with a radially projecting annular collar adapted to limit penetration of the one end into the respective vertebra. Alternately at least one of the outer ends is formed with a sharp edge.

BRIEF DESCRIPTION OF THE DRAWING

The above and other objects, features, and advantages will become more readily apparent from the following description, reference being made to the accompanying drawing in which:

FIGS. 7, 8, and 9 are cross sections taken respectively along lines VII—VII, VIII—VIII, and IX—IX of FIG. 6;

FIG. 10 is a view like FIG. 5 of another end element in accordance with this invention;

FIG. 11 is a cross section taken along line XI—XI of FIG. 10; and

FIG. 12 is an axial section taken along line XII—XII of FIG. 11.

SPECIFIC DESCRIPTION

Figure 1:
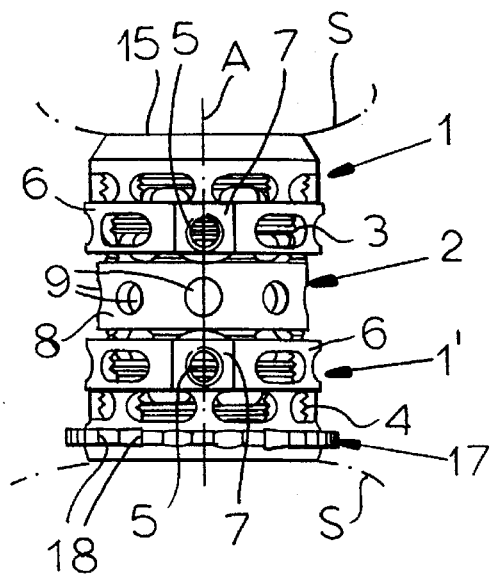
FIG. 1 is a side view of an implant according to this invention.
Figure 2:
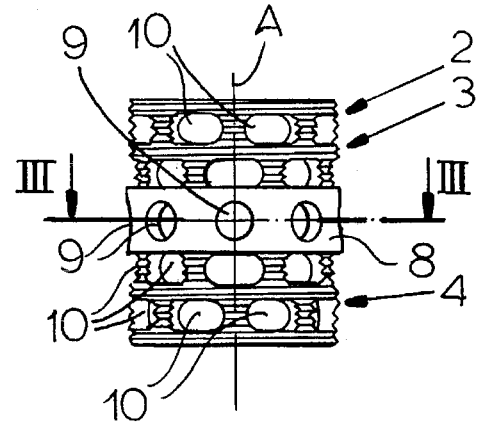
FIG. 2 is a side view of the center element.
Figure 3:
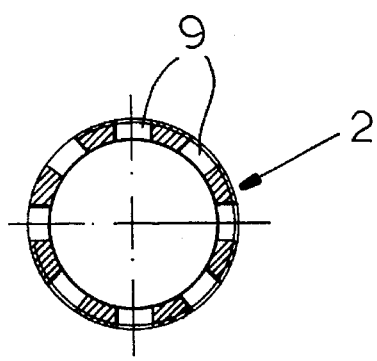
FIG. 3 is a cross section taken along line III—III of FIG. 2.

As seen in FIGS. 1–3 and 10–12, a spinal implant intended for engagement between two opposing vertebral surfaces indicated schematically at S is centered on an axis A and comprises a pair of tubular end elements 1 and 1' and a tubular center element 2, all formed of a biologically inert metal, typically a steel alloy. The center body 2 as shown in FIG. 2 has upper and lower external screwthreads 3 and 4 of opposite hand that mesh with complementary internal screwthreads of the respective elements 1 and 1'.

The upper and lower end elements 1 and 1' are formed at their confronting inner ends each with a thickened outwardly projecting collar 6 and at one or more locations on this collar 6 with a thickened region 7 which in turn is formed with a radially throughgoing threaded bore 5. A setscrew shown at 19 in FIG. 11 can be threaded into this hole to lock the element 1 or 1" on the element 2 against relative angular movement.

The center element 1 is formed with a thickened center region 8 that is clear of screwthreads and that is formed with an array of angularly equispaced and radially throughgoing circular holes or bores 9. A tool with a simple cylindrical end can be inserted into any of these holes 9 to rotate the center element 2 relative to the end elements 1 and 1' so as to increase or decrease the overall axial length of the implant.

The elements 1 and 1' have outer ends formed as sharp edges 15. In addition the lower element 1' is provided above its sharp edge 15 with a radially outwardly projecting stop collar 17 formed with notches so that it can be held easily and so that this collar 17 can limit penetration of the element 1' into bone tissue. If extreme force had to be brought to bear, the outer end of the element 1' could be closed with a perforated plate to get a broader purchase on the vertebral surface. The collar 17 could project radially inward where space is tight.

Figure 4:
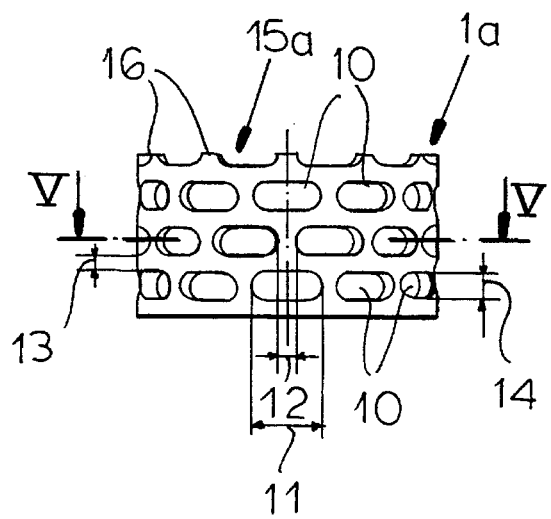
FIG. 4 is a slightly enlarged view of the upper end element of the implant.
Figure 5:
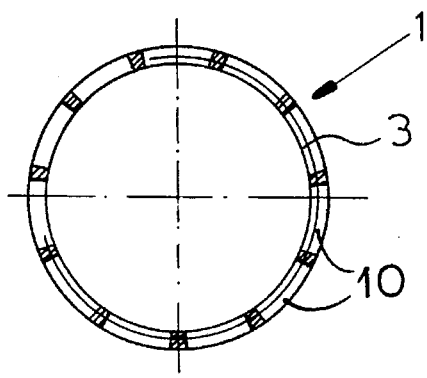
FIG. 5 is a cross section taken along line V—V of FIG. 4
Figure 6:
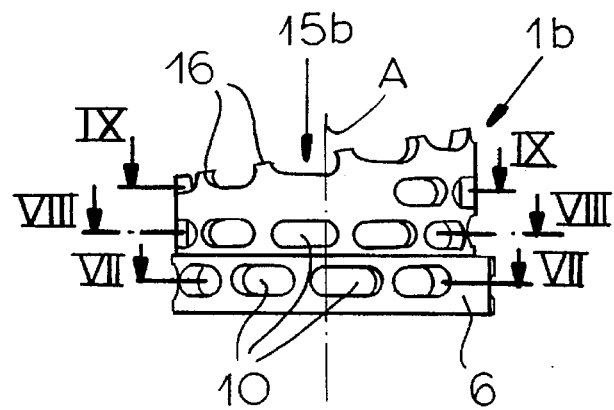
FIG. 6 is a view like FIG. 5 of another end element according to the invention.
Figure 7:
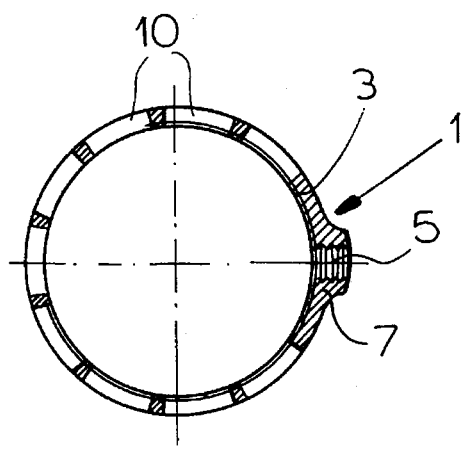
Figure 8:
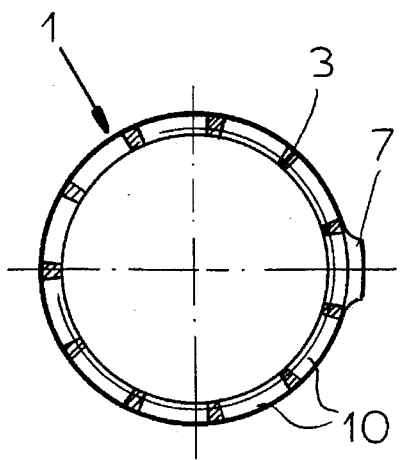

FIGS. 4 and 5 show an end element 1a generally identical to the element 1, but instead having an upper edge 15a formed with teeth 16 so it can dig into a bone it is set on.

In FIGS. 6 through 9 an end element 1b is shown having an upper edge 15b that has teeth 16 and lies on a plane that is skew to the axis A. Such an implant element 1b can be used for correcting scoliosis or a similar orthopedic defect.

All the elements 1, 1' and 2 are formed with arrays of radially throughgoing elongated apertures 10. FIG. 4 shows how each of the apertures 10 has a horizontal width 11 that is at least twice its vertical width 14. The apertures 10 are arranged in staggered rows spaced axially by a spacing 13 equal to at most the minor-axis height 14 and spaced within the rows by a distance 12 also equal to at most half the major-axis width 11. Thus each of the holes 10 in an end element 1, 1', 1a, or 1b will always overlap with at least one of the holes 10 of the element 2, as the vertical and horizontal spacing between these holes 10 is less than half the respective dimensions of the holes. As a result if the passage formed by the tubular implant is filled with bone cement and/or bone fragments before installation, good bone growth around and through this implant is insured.

I claim:

1. A spinal implant for engagement in a space left by ablation of a vertebral body between a pair of adjacent vertebrae, the implant comprising:

a tubular center element extending along an axis, having upper and lower ends formed with respective upper and lower external screwthreads of opposite hand, and formed with a plurality of radially throughgoing apertures; and respective upper and lower tubular end elements each formed with a plurality of radially throughgoing apertures, axially flanking the center element, each having an internally threaded circular-section inner end threaded onto a respective one of the external screwthreads and radially surrounding the respective upper and lower ends of the center element, and each having an outer end adapted to bear on a respective one of the adjacent vertebrae, all the apertures being so positioned and dimensioned that when the end elements are threaded to the center element each center-element aperture in a region of axial overlap between the elements is at least partially radially aligned with one of the respective end-element apertures.

2. The spinal implant defined in claim 1 wherein one of the end elements is formed at its inner end with a radially throughgoing threaded bore, the implant further comprising a setscrew threaded in the bore and bearing radially on the center element.

3. The spinal implant defined in claim 2 wherein the one end element has a thickened region surrounding the bore.

4. The spinal implant defined in claim 2 wherein the one end element is formed with a circumferential thickened region through which the bore extends.

5. The spinal implant defined in claim 1 wherein the center element has between the screwthreads a threadfree portion formed with some of the apertures.

6. The spinal implant defined in claim 5 wherein the apertures in the thread-free portion are substantially circular.

7. The spinal implant defined in claim 1 wherein the apertures of the end elements are elongated angularly and radially traverse the respective screwthreads.

8. The spinal implant defined in claim 7 wherein all of the apertures have major axes lying in planes perpendicular to the axis.

9. The spinal implant defined in claim 1 wherein the apertures of each element are arrayed in rows each centered on a respective plane perpendicular to the axis and the apertures of each row are offset angularly from the apertures of adjacent rows.

10. The spinal implant defined in claim 1 wherein each aperture has a major axis lying in a plane perpendicular to the axis and a minor axis parallel to the axis, each major axis being at least twice as long as the respective minor axis.

11. The spinal implant defined in claim 10 wherein all of the apertures are arranged in rows lying in the respective planes and the axial spacing between each row and the adjacent rows is equal to about half the axial length of the respective minor axes.

12. The spinal implant defined in claim 1 wherein the outer end of one of the end elements has an edge lying in a plane forming an acute angle with the axis.

13. The spinal implant defined in claim 1 wherein the outer end of at least one of the end elements is formed with an annular array of teeth adapted to dig into the respective vertebra.

14. The spinal implant defined in claim 13 wherein the outer end of the one end element is formed between the teeth with outwardly open notches.

15. The spinal implant defined in claim 13 wherein the one end element is formed with a radially projecting annular collar adapted to limit penetration of the one end element into the respective vertebra.

16. The spinal implant defined in claim 1 wherein at least one of the outer ends is formed as a sharp edge.

17. The spinal implant defined in claim 1 wherein the elements are made of metal.

18. The spinal implant defined in claim 1 wherein the elements form an axially throughgoing passage.

* * * * *